(12) United States Patent
Green et al.

(10) Patent No.: US 9,155,530 B2
(45) Date of Patent: Oct. 13, 2015

(54) SPECIALLY DESIGNED MAGNESIUM-ALUMINUM ALLOYS AND MEDICAL USES THEREOF IN A HEMODYNAMIC ENVIRONMENT

(75) Inventors: Stephen M. Green, Syracuse, NY (US); Rudolph Buchheit, Columbus, OH (US)

(73) Assignee: Transluminal Technologies, LLC, Syracuse, NY (US)

( * ) Notice: Subject to any disclaimer, the term of this patent is extended or adjusted under 35 U.S.C. 154(b) by 405 days.

(21) Appl. No.: 13/292,960

(22) Filed: Nov. 9, 2011

(65) Prior Publication Data

US 2012/0116446 A1 May 10, 2012

Related U.S. Application Data

(60) Provisional application No. 61/411,698, filed on Nov. 9, 2010.

(51) Int. Cl.
*A61F 2/06* (2013.01)
*A61B 17/00* (2006.01)
*A61L 27/04* (2006.01)
*A61L 31/02* (2006.01)

(52) U.S. Cl.
CPC ............ *A61B 17/0057* (2013.01); *A61L 27/047* (2013.01); *A61L 31/022* (2013.01); *A61B 2017/00831* (2013.01)

(58) Field of Classification Search
CPC .................. A61B 17/0057; A61B 2017/00831; A61L 31/022

USPC ............... 623/1.38, 23.72; 606/213, 215, 151
See application file for complete search history.

(56) References Cited

U.S. PATENT DOCUMENTS

| | | | |
|---|---|---|---|
| 3,099,083 A * | 7/1963 | De Long | ......................... 29/458 |
| 4,744,364 A | 5/1988 | Kensey | |
| 4,890,612 A | 1/1990 | Kensey et al. | |
| 5,222,974 A | 6/1993 | Kensey et al. | |
| 5,282,827 A | 2/1994 | Kensey et al. | |
| 5,312,435 A | 5/1994 | Nash et al. | |
| 5,342,393 A | 8/1994 | Stack | |
| 5,350,399 A | 9/1994 | Erlebacher et al. | |
| RE34,866 E | 2/1995 | Kensey et al. | |
| 5,391,182 A | 2/1995 | Chin | |

(Continued)

FOREIGN PATENT DOCUMENTS

| | | |
|---|---|---|
| JP | 2009522067 A | 6/2009 |
| JP | 54-113288 | 5/2012 |

(Continued)

OTHER PUBLICATIONS

G.M. Abady, N.H. Hilal, M. El-Rabiee, W.A. Badawy, Electrochim. Acta, 55, 6651-6658 (2010).

(Continued)

*Primary Examiner* — Victor Nguyen
(74) *Attorney, Agent, or Firm* — Frederick J. M. Price; George R. McGuire; Bond Schoeneck & King, PLLC

(57) ABSTRACT

The present invention relates generally to specially designed magnesium-aluminum ("Mg—Al") alloys and medical uses thereof in a hemodynamic environment, and, more particularly to devices for sealing an opening formed through biological tissue (such as blood vessels) made from such specially designed magnesium-aluminum alloys.

9 Claims, 10 Drawing Sheets

(56) References Cited

U.S. PATENT DOCUMENTS

| | | |
|---|---|---|
| 5,411,520 A | 5/1995 | Nash et al. |
| 5,441,517 A | 8/1995 | Kensey et al. |
| 5,531,759 A | 7/1996 | Kensey et al. |
| 5,545,178 A | 8/1996 | Kensey et al. |
| 5,593,422 A | 1/1997 | Muijs Van de Moer et al. |
| 5,641,501 A | 6/1997 | Cooper et al. |
| 5,645,566 A | 7/1997 | Brenneman et al. |
| 5,649,959 A | 7/1997 | Hannam et al. |
| 5,662,681 A | 9/1997 | Nash et al. |
| 5,676,689 A | 10/1997 | Kensey et al. |
| 5,690,674 A | 11/1997 | Diaz |
| 5,700,277 A | 12/1997 | Nash et al. |
| 5,707,393 A | 1/1998 | Kensey et al. |
| 5,725,553 A | 3/1998 | Moenning |
| 5,782,861 A | 7/1998 | Cragg et al. |
| 5,861,004 A | 1/1999 | Kensey et al. |
| 5,916,236 A | 6/1999 | Muijs Van de Moer et al. |
| 5,935,147 A | 8/1999 | Kensey et al. |
| 5,941,898 A | 8/1999 | Moenning et al. |
| 5,984,950 A | 11/1999 | Cragg et al. |
| 6,007,563 A | 12/1999 | Nash et al. |
| 6,017,359 A | 1/2000 | Gershony et al. |
| 6,045,569 A | 4/2000 | Kensey et al. |
| 6,059,816 A | 5/2000 | Moenning |
| 6,071,300 A | 6/2000 | Brenneman et al. |
| 6,080,183 A | 6/2000 | Tsugita et al. |
| 6,090,130 A | 7/2000 | Nash et al. |
| 6,113,624 A | 9/2000 | Bezwada et al. |
| 6,162,192 A | 12/2000 | Cragg et al. |
| 6,179,863 B1 | 1/2001 | Kensey et al. |
| 6,190,400 B1 | 2/2001 | Van de Moer et al. |
| 6,197,042 B1 | 3/2001 | Ginn et al. |
| 6,277,140 B2 | 8/2001 | Ginn et al. |
| 6,287,332 B1 | 9/2001 | Bolz et al. |
| 6,315,753 B1 | 11/2001 | Cragg et al. |
| 6,368,341 B1 | 4/2002 | Abrahamson |
| 6,371,974 B1 | 4/2002 | Brenneman et al. |
| 6,391,048 B1 | 5/2002 | Ginn et al. |
| 6,425,911 B1 | 7/2002 | Akerfeldt et al. |
| 6,461,364 B1 | 10/2002 | Ginn et al. |
| 6,508,828 B1 | 1/2003 | Akerfeldt et al. |
| 6,527,734 B2 | 3/2003 | Cragg et al. |
| 6,540,735 B1 | 4/2003 | Ashby et al. |
| 6,544,236 B1 | 4/2003 | Cragg et al. |
| 6,610,026 B2 | 8/2003 | Cragg et al. |
| 6,623,509 B2 | 9/2003 | Ginn |
| 6,632,238 B2 | 10/2003 | Ginn et al. |
| 6,656,207 B2 | 12/2003 | Epstein et al. |
| 6,663,655 B2 | 12/2003 | Ginn et al. |
| 6,712,837 B2 | 3/2004 | Akerfeldt et al. |
| 6,749,621 B2 | 6/2004 | Pantages et al. |
| 6,764,500 B1 | 7/2004 | Muijs Van de Moer et al. |
| 6,780,197 B2 | 8/2004 | Roe et al. |
| 6,786,915 B2 | 9/2004 | Akerfeldt et al. |
| 6,846,319 B2 | 1/2005 | Ginn et al. |
| 6,860,895 B1 | 3/2005 | Akerfeldt et al. |
| 6,863,680 B2 | 3/2005 | Ashby |
| 6,890,343 B2 | 5/2005 | Ginn et al. |
| 6,896,692 B2 | 5/2005 | Ginn et al. |
| 6,942,674 B2 | 9/2005 | Belef et al. |
| 6,964,658 B2 | 11/2005 | Ashby et al. |
| 6,969,397 B2 | 11/2005 | Ginn |
| 7,001,398 B2 | 2/2006 | Carley et al. |
| 7,001,411 B1 | 2/2006 | Dean |
| 7,008,440 B2 | 3/2006 | Sing et al. |
| 7,029,489 B1 | 4/2006 | Ashby et al. |
| 7,037,322 B1 | 5/2006 | Sing et al. |
| 7,048,710 B2 | 5/2006 | Cragg et al. |
| 7,083,635 B2 | 8/2006 | Ginn |
| 7,201,725 B1 | 4/2007 | Cragg et al. |
| 7,250,057 B2 | 7/2007 | Forsberg |
| 7,267,679 B2 | 9/2007 | McGuckin, Jr. |
| 7,326,230 B2 | 2/2008 | Ravikumar |
| D566,272 S | 4/2008 | Walburg et al. |
| 7,361,183 B2 | 4/2008 | Ginn |
| 2001/0003158 A1 | 6/2001 | Kensey |
| 2002/0004060 A1 | 1/2002 | Heublein |
| 2002/0198562 A1 | 12/2002 | Akerfeldt |
| 2003/0023267 A1 | 1/2003 | Ginn |
| 2003/0144695 A1 | 7/2003 | McGuckin |
| 2004/0019330 A1 | 1/2004 | Ashby |
| 2004/0093025 A1 | 5/2004 | Egnelov |
| 2004/0153122 A1 | 8/2004 | Palermo |
| 2004/0153123 A1 | 8/2004 | Palermo |
| 2004/0215231 A1 | 10/2004 | Fortune |
| 2004/0215232 A1 | 10/2004 | Belhe |
| 2005/0085773 A1 | 4/2005 | Forsberg |
| 2005/0085853 A1 | 4/2005 | Forsberg |
| 2005/0090859 A1 | 4/2005 | Ravikumar |
| 2005/0096696 A1 | 5/2005 | Forsberg |
| 2005/0096697 A1 | 5/2005 | Forsberg |
| 2005/0107820 A1 | 5/2005 | Forsberg |
| 2005/0107827 A1 | 5/2005 | Paprocki |
| 2005/0125030 A1 | 6/2005 | Forsberg |
| 2005/0177189 A1 | 8/2005 | Ginn |
| 2005/0192627 A1 | 9/2005 | Whisenant |
| 2005/0192661 A1 | 9/2005 | Griffen |
| 2005/0222614 A1 | 10/2005 | Ginn |
| 2005/0234396 A1 | 10/2005 | Forsberg |
| 2005/0267528 A1 | 12/2005 | Ginn |
| 2005/0273135 A1 | 12/2005 | Chanduszko |
| 2005/0273136 A1 | 12/2005 | Belef |
| 2006/0018954 A1 | 1/2006 | Kuttler |
| 2006/0020315 A1 | 1/2006 | Geistert |
| 2006/0052824 A1 | 3/2006 | Ransick |
| 2006/0052825 A1 | 3/2006 | Ransick et al. |
| 2006/0052863 A1 | 3/2006 | Harder |
| 2006/0052864 A1 | 3/2006 | Harder |
| 2006/0058844 A1 | 3/2006 | White |
| 2006/0064160 A1 | 3/2006 | Gerold |
| 2006/0106418 A1 | 5/2006 | Seibold |
| 2006/0135991 A1 | 6/2006 | Kawaura |
| 2006/0142797 A1 | 6/2006 | Egnelov |
| 2006/0155327 A1 | 7/2006 | Briganti |
| 2006/0195123 A1 | 8/2006 | Ginn |
| 2006/0195124 A1 | 8/2006 | Ginn |
| 2006/0206146 A1 | 9/2006 | Tenerz |
| 2006/0229670 A1 | 10/2006 | Bates et al. |
| 2006/0229672 A1 | 10/2006 | Forsberg |
| 2006/0229673 A1 | 10/2006 | Forsberg |
| 2006/0229674 A1 | 10/2006 | Forsberg |
| 2006/0253037 A1 | 11/2006 | Ginn |
| 2006/0265007 A1 | 11/2006 | White |
| 2006/0287710 A1 | 12/2006 | Lendlein |
| 2007/0010853 A1 | 1/2007 | Ginn |
| 2007/0032823 A1 | 2/2007 | Tegg |
| 2007/0032824 A1 | 2/2007 | Terwey |
| 2007/0050009 A1 | 3/2007 | Flanagan |
| 2007/0055305 A1 | 3/2007 | Schnyder |
| 2007/0073345 A1 | 3/2007 | Pipenhagen |
| 2007/0135842 A1 | 6/2007 | Van de Moer |
| 2007/0156084 A1 | 7/2007 | Belhe |
| 2007/0250080 A1 | 10/2007 | Jones |
| 2007/0255314 A1 | 11/2007 | Forsberg |
| 2007/0270904 A1 | 11/2007 | Ginn |
| 2007/0270940 A1 | 11/2007 | Doty |
| 2007/0276433 A1 | 11/2007 | Huss |
| 2007/0282352 A1 | 12/2007 | Carley |
| 2007/0282432 A1 | 12/2007 | Stinson |
| 2008/0033535 A1 | 2/2008 | Mueller |
| 2008/0033538 A1 | 2/2008 | Borck |
| 2008/0058923 A1 | 3/2008 | Bertsch |
| 2008/0065151 A1 | 3/2008 | Ginn |
| 2008/0071311 A1 | 3/2008 | White |
| 2009/0069844 A1* | 3/2009 | Green et al. ............ 606/213 |
| 2010/0179589 A1 | 7/2010 | Roorda et al. |
| 2011/0046665 A1 | 2/2011 | Green et al. |

FOREIGN PATENT DOCUMENTS

| | | |
|---|---|---|
| JP | 2013538865 | 10/2013 |
| KR | 1020090086590 | 10/2009 |
| WO | WO2006110614 A2 | 10/2006 |
| WO | WO2006124245 A2 | 11/2006 |

(56) References Cited

FOREIGN PATENT DOCUMENTS

| WO | WO2006124251 A2 | 11/2006 |
|---|---|---|
| WO | WO2007081448 A2 | 7/2007 |
| WO | WO2007082147 A2 | 7/2007 |
| WO | WO2007139755 A2 | 12/2007 |
| WO | 2008/035948 | 3/2008 |
| WO | WO2009035921 A2 | 3/2009 |
| WO | 2009/117241 | 9/2009 |
| WO | WO2009116799 A2 | 9/2009 |
| WO | 2009/148515 | 12/2009 |

OTHER PUBLICATIONS

Joseph R. Davis, Metals Handbook, Corrosion of Magnesium and Magnesium Alloys, Figure 1, p. 741.
PCT International Search Report dated May 16, 2012, International Application No. PCT/US2011/058936.
Abady, G., Hilal, N., El-Rabiee, M., Badawy, W., Effect of Al Content on the Corrosion Behavior of Mg-Al Alloys in Aqueous Solutions of Different pH, Electrochimica Acta, 2010, pp. 6651-6658, vol. 55.
Hawke, D., Hillis, J., Pekguleryuz, M., Nakatsugawa, I., Corrosion Behavior.
He, Y., Tao, H., Zhang, Y., Jiang, Y., Zhang, S., Zhao, C., Li, J., Zhang, B., Song, Y., Zhang, X., Biocompatability of Bio-Mg-Zn Alloy Within Bone with Heart, Liver, Kidney, and Spleen, Chinese Science Bulletin, 2009, pp. 484-491, vol. 54, No. 3.
Hiromoto, S., Yamamoto, A., Corrosion Behavior of Anodized Bioabsorbable Magnesium in Medium, National Institute for Materials Science.
Corrosion and Finishing of Magnesium Alloys.
Kim, S.J., Okido, M., The Electrochemical Properties and Mechanism of Formation of Anodic Oxide Films on Mg-Al Alloys, Bull. Korean Chem. Soc., 2003, p. 975, vol. 24, No. 8.
Medved, J., Mrvar, P., Voncina, M., Oxidation Resistance of AM60, AM50, AE42 and AZ91 Magnesium Alloys, Intechopen.
Persaud-Sharma, D., Budiansky, N., McGoron, A., Mechanical Properties and Tensile Failure Analysis of Novel Bio-Absorbable Mg-Zn-Cu and Mg-Zn-Se Alloys for Endovascular Applications, Metals, 2013, pp. 23-40, vol. 3.
Sudholz, A., Birbilis, N., Bettles, C., Gibson, M., Corrosion Behaviour of Mg-Alloy AZ91E with Atypical Alloying Additions, Journal of Alloys and Compounds, 2008.
Van Agterveld, D., Palasantzas, G., De Hossen, T., Magnesium Surface Segregation and Oxidation in Al-Mg Alloys Studied with Local Probe Scanning Auger-Scanning Electron Microscopy, Applied Surface Science, 1999, pp. 250-258, vol. 152.
Wang, Q., Tan, L., Xu, W., Zhang, B., Yang, K., Dynamic Behaviors of a Ca-P Coated AZ31B Magnesium Alloy During In Virto and In Vivo Degradations, Materials Science and Engineering B, 2011, pp. 1718-1726, vol. 176.
Yamauchi, K., Asakura, S., Galvanic Dissolution Behavior of Magnesium-1 mass % Magnesium-0.5 mass % calcium Alloy Anode for Cathodic Protection in Fresh Water, Materials Transactions, 2003, pp. 1046-1048, vol. 44, No. 5.
Abady, G., Hilal, N., El-Rabiee, M., Badawy, W., Effect of Al Content on the Corrosion Behavior of Mg-Al Alloys in Aqueous Solutions of Different pH, Electrochimica Acta, 2010, pp. 6651-6658, vol. 55.
Del Gaudio, C., Bagala, P., Venturini, M., Grandi, C., Parnigotto, P., Bianco, A., Montesperelli, G., Assessment of in Vitro Temporal Corrosion and Cytotoxicity of AZ91D Alloy, J. Mater Sci: Mater Med, 2012, pp. 2553-2562, vol. 23.
Feliu Jr., S., Galvan, J.C., Pardo, A., Merino, M.C., Arrabal, R., Native Air-Formed Oxide Film and its Effect on Magnesium Alloys Corrosion, The Open Corrosion Journal, 2010, pp. 80-91, vol. 3.
Feliu Jr., S., Samaniego, A., Bermudez, E., El-Hadad, A., Llorente, I., Galvan, J., Effect of Native Oxide Film on Commercial Magnesium Alloys Substrates and Carbonate Conversion Coating Growth and Corrosion Resistance, Materials, 2014.
Gu, X., Zheng, Y., Cheng, Y., Zhong, S., Xi, T., In Vitro Corrosion and Biocompatibility of Binary Magnesium Alloys, Biomaterials, 2009, pp. 484-498, vol. 30.

Gu, X.N., Zheng, Y.F., A Review on Magnesium Alloys as Biodegradable Materials, Front. Mater. Sci. China, 2010, pp. 111-115, vol. 4(2).
Hawke, D., Hillis, J., Pekguleryuz, M., Nakatsugawa, I., Corrosion Behavior, (2010).
He, Y., Tao, H., Zhang, Y., Jiang, Y., Zhang, S., Zhao, C., Li, J., Zhang, B., Song, Y., Zhang, X., Biocompatability of Bio-Mg-Zn Alloy Within Bone with Heart, Liver, Kidney, and Spleen, Chinese Science Bulletin, 2009, pp. 484-491, vol. 54, No. 3.
Heublein, B., Rohde, R., Kaese, V., Niemeyer, M., Hartung, W., Haverich, A., Biocorrosion of Magnesium Alloys: A New Principle in Cardiovascular Implant Technology, Heart, 2003, pp. 651-656, vol. 89.
Hiromoto, S., Yamamoto, A., Corrosion Behavior of Anodized Bioabsorbable Magnesium in Medium, National Institute for Materials Science, (2003).
Corrosion and Finishing of Magnesium Alloys, (2003).
Kim, S.J., Okido, M., The Electrochemical Properties and Mechanism of Formation of Anodic Oxide Films on Mg-Al Alloys, Bull. Korean Chem. Soc., 2003, p. 975, vol. 24, No. 8.
Kirkland, N., Lespagnol, J., Birbilis, N., Staiger, M., A Survey of Bio-Corrosion Rates of Magnesium Alloys, Corrosion Science, 2010, pp. 287-291, vol. 52.
Levesque, J., Hermawan, H., Dube, D., Mantovani, D., Design of a Pseudo-Psychological Test Bench Specific to the Development of Biodegradable Metallic Biomaterials, Acta Biomaterialia, 2008, pp. 284-295, vol. 4.
Medved, J., Mrvar, P., Voncina, M., Oxidation Resistance of AM60, AM50, AE42 and AZ91 Magnesium Alloys, Intechopen, (2008).
Moravej, M., Mantovani, D., Biodegradable Metals for Cardiovascular Stent Application: Interests and New Opportunities, International Journal of Molecular Sciences, 2011, pp. 4250-4270, vol. 12.
Morozova, G., Magnesium and Magnesium Alloys, Metal Science and Heat Treatment, 2008, vol. 50, Nos. 3-4.
Muller, W., Nascimento, M., Zeddies, M., Corsico, M., Magnesium and its Alloys as Degradable Biomaterials. Corrosion Studies Using Potentiodynamic and EIS Electrochemical Techniques, Materials Research, 2007, pp. 5-10, vol. 10, No. 1.
Narayanan, T., Park, I., Lee, M., Strategies to Improve the Corrosion Resistance of Mocroarc Oxidation (MAO) Coated Magnesium Alloys for Degradable Implants: Prospects and Challenges, Progress in Materials Science, 2014, pp. 1-71, vol. 60.
Pardo, A., Merino, M., Coy, A., Viejo, F., Arrabal, R., Feliu Jr., S., Influence of Microstructure and Composition on the Corrosion Behaviour of Mg/Al Alloys in Chlorine Media, Electrochimica Acta, 2008, pp. 7890-7902, vol. 53.
Persaud-Sharma, D., Mcgoron, A., Biodegradable Magnesium Alloys: A Review of Material Development and Applications, Journal of Biomimetics, Biomaterials and Tissue Engineering, 2011, vol. 12.
Persaud-Sharma, D., Budiansky, N., Mcgoron, A., Mechanical Properties and Tensile Failure Analysis of Novel Bio-Absorbable Mg-Zn-Cu and Mg-Zn-Se Alloys for Endovascular Applications, Metals, 2013, pp. 23-40, vol. 3.
Poinern, G., Brundavanam, S., Fawcett, D., Biomedical Magnesium Alloys: A Review of Material Properties, Surface Modifications and Potential as a Biodegradable Orthopaedic Implant, American Journal of Biomedical Engineering, 2012, pp. 218-240, vol. 2(6).
Shaw, B., Corrosion Resistance of Magnesium Alloys, Corrosion: Fundamentals, Testing and Protection, 2003, vol. 13A.
Shaw, B., Sikora, E., Virtanen, S., Fix, Heal, and Disappear: A New Approach to Using Metals in the Human Body, The Electrochemical Society, 2008.
Song, G., Atrens, A., Wu, X., Zhang, B., Corrosion Behaviour of AZ21, AZ501 and AZ91 in Sodium Chloride, Corrosion Science, 1998, pp. 1769-1791, vol. 40, No. 10.
Song, G., Atrens, A., Corrosion Mechanisms of Magnesium Alloys, Advanced Engineering Materials, 1999, vol. 1.
Song, G., Atrens, A., Dargusch, M., Influence of Microstructure on the Corrosion of Diecast AS91D, Corrosion Science, 1999, pp. 249-273, vol. 41.

(56) References Cited

OTHER PUBLICATIONS

Staiger, M., Peitak, A., Huadmai, J., Dias, G., Magnesium and its Alloys as Orthopedic Biomaterials: A Review, Biomaterials, 2006, pp. 1728-1734, vol. 27.

Sudholz, A., Birbilis, N., Bettles, C., Gibson, M., Corrosion Behaviour of Mg—Alloy AZ91E with Atypical Alloying Additions, Journal of Alloys and Compounds, 2008.

Van Agterveld, D., Palasantzas, G., De Hossen, T., Magnesium Surface Segregation and Oxidation in Al—Mg Alloys Studied with Local Probe Scanning Auger-Scanning Electron Microscopy, Applied Surface Science, 1999, pp. 250-258, vol. 152.

Wan, G., Maitz, M., Sun, H., Li, P., Huang, N., Corrosion Properties of Oxygen Plasma Immersion Ion Implantation Treated Magnesium, Surface & Coatings Technology, 2007, pp. 8267-8272, vol. 201.

Wang, Q., Tan, L., Xu, W., Zhang, B., Yang, K., Dynamic Behaviors of a Ca—P Coated AZ31B Magnesium Alloy During in Virto and in Vivo Degradations, Materials Science and Engineering B, 2011, pp. 1718-1726, vol. 176.

Wen, Z., Wu, C., Dai, C., Yang, F., Corrosion Behaviors of Mg and its Alloys with Different Al Contents in a Modified Simulated Body Fluid, Journal of Alloys and Compounds, 2009, pp. 392-399, vol. 488.

Williams, D., New Interests in Magnesium, Medical Device Technology, 2006, p. 9, vol. 17, No. 3.

Witte, F., Hort, N., Vogt, C., Cohen, S., Kainer, K., Willumeit, R., Feyerabend, F., Degradable Biomaterials Based on Magnesium Corrosion, Current Opinion in Solid State and Materials Science, 2008, pp. 63-72, vol. 12.

Witte, F., The History of Biodegradable Magnesium Implants: A Review, Acta Biomaterialia, 2010, pp. 1680-1692, vol. 6.

Yamauchi, K., Asakura, S., Galvanic Dissolution Behavior of Magnesium—1 mass % Magnesium—0.5 mass % calcium Alloy Anode for Cathodic Protection in Fresh Water, Materials Transactions, 2003, pp. 1046-1048, vol. 44, No. 5.

Zhang, J., Wu, C., Corrosion and Protection of Magnesium Alloys—A Review of the Patent Literature, Recent Patents in Corrosion Science, 2010, pp. 55-68, vol. 2.

A. Pardo, M.C. Merino, A.E. Coy, F. Viejo, R. Arraabal, S. Feliu, Jr., Electrochim. Acta, 53, 7890-7902 (2008).

G.M. Abady, N. H. Hilal, M. El-Rabiee, W.A. Badawy, Electrochim. Acta, 55, 6651-6658 (2010).

Z. Wen, C. Wu, C. Dai, F. Yang, Alloys and Compounds, 488, 392-399 (2009).

N. T. Kirkland, J. Lespagnol, N. Birbilis, M.P. Staiger, Corrosion Sci., 52, 287-291 (2010).

R.K. Singh Raman, N. Birbilis, J. Efthimiadis, Corrosion Engineering Science and Technology, vol. 39, No. 4, p. 346 (2004).

Joseph R. Davis, Metals Handbook, Corrosion of Magnesium and Magnesium Alloys, Figure 1, p. 741, (2004).

\* cited by examiner

Left femoral, 4 hrs
a.

Right femoral, 4 hrs
c.

Left femoral, 8 hrs
b.

Right femoral, 8 hrs
d.

SPECIALLY DESIGNED MAGNESIUM-ALUMINUM ALLOYS AND MEDICAL USES THEREOF IN A HEMODYNAMIC ENVIRONMENT

RELATED APPLICATION DATA

The present application claims priority to U.S. provisional patent application No. 61/411,698, filed on Nov. 9, 2010; all of the foregoing patent-related document(s) are hereby incorporated by reference herein in their respective entirety(ies).

BACKGROUND OF THE INVENTION

1. Field of Invention

The present invention relates generally to specially designed magnesium-aluminum ("Mg—Al") alloys and medical uses thereof in a hemodynamic environment, and, more particularly to devices for sealing an opening formed through biological tissue (such as blood vessels) made from such specially designed magnesium-aluminum alloys.

2. Description of the Related Art

Certain Mg alloys are known and have been used to form devices for sealing an opening formed through biological tissue (such as blood vessels). See, e.g., U.S. Pat. Pub. No. 20110046665, paras. [0015], [0018], [0025], and [0038] (describing a closure device for sealing an opening formed through biological tissue which comprises a footplate, a plug, and a wire, and where the footplate, wire, and/or plug portion is made from a biocompatible and biocorrodible metal comprising certain magnesium alloys).

Aluminum additions to Mg have a significant effect on corrosion rate, though a variety of trends can be found. Pardo reports that a 3% Al addition in Mg alloy AZ31 slightly decreases corrosion rate in 3.5% NaCl solution and that Al additions of 8 to 9 wt. % found in AM80 and AZ91 strongly reduce corrosion rate in electrochemical testing in 3.5% NaCl solution (See A. Pardo, M. C. Merino, A. E. Coy, F. Viejo, R. Arrabal, S. Feliu, Jr., Electrochim. Acta, 53, 7890-7902 (2008)). Abady and co-workers found in electrochemical studies of alloys from 0 to 15 wt. % Mg exposed to chloride-free buffer solutions that corrosion rate peaked at 5 wt. % Al and decreased significantly in alloys with 10 and 15% Al (See G. M. Abady, N. H. Hilal, M. El-Rabiee, W. A. Badawy, Electrochim. Acta, 55, 6651-6658 (2010)). Kita et al. found from electrochemical testing that corrosion rate increases in dilute chloride environments with increasing Al content over the range of 1 to 9 mass percent (See H. Kita, M. Kimoto, T Kudo, J. Japan Inst. Of Metals, 69, 805-809 (2005)).

In simulated biological environments, the corrosion rate dependence appears to indicate that increasing Al content decreases rate. From electrochemical corrosion rate determinations of Mg-xAl-3Zn alloys exposed to quiescent modified simulated body fluid (SBF) at 36.5° C., corrosion rates were found to decrease strongly with increasing Al content (See Z. Wen, C. Wu, C. Dai, F. Yang, J. Alloys and Compounds, 488, 392-399 (2009)). Kirkland reported corrosion rates in Minimal Essential Medium (MEM) at 37° C. showing strongly decreased corrosion rate with increasing Al concentration over the range of 0 to 9 weight percent (See N. T. Kirkland, J. Lespagnol, N. Birbilis, M. P. Staiger, Corrosion Sci., 52, 287-291 (2010)).

Description of the Related Art Section Disclaimer: To the extent that specific patents/publications are discussed above in this Description of the Related Art Section or elsewhere in this Application, these discussions should not be taken as an admission that the discussed patents/publications are prior art for patent law purposes. For example, some or all of the discussed patents/publications may not be sufficiently early in time, may not reflect subject matter developed early enough in time and/or may not be sufficiently enabling so as to amount to prior art for patent law purposes. To the extent that specific patents/publications are discussed above in this Description of the Related Art Section and/or throughout the application, they are all hereby incorporated by reference into this document in their respective entirety(ies).

SUMMARY OF THE INVENTION

The present invention recognizes that there are potential problems and/or disadvantages with the conventional Mg—Al alloys and the unhelpful disparate results from the studies performed regarding these alloys referenced in the Description of the Related Art Section above. See FIG. 1 (The Singh reference cited in this figure and other figures is R. K. Singh Raman, N. Birbilis, J. Efthimiadis, Corrosion Engineering Science and Technology, Vol. 39, no. 4, p. 346 (2004); the remainder of the cited references in this figure and other figures herein are already referenced in this application). The apparently disparate findings is that the corrosion rate of Mg—Al alloys likely depends not just on the Al content, but on other factors such as the presence of other alloying elements, and the alloy microstructure. It is also likely to depend on the environment composition, pH, temperature, and in this particular case, flow rate of the contacting liquid medium. There is a need to determine whether SBF and MEM environments adequately mimic the mechanically dynamic physiological environment inside blood vessels. There is also a need to develop Mg—Al alloys that can be tuned to corrode at a particular predictable rate in a hemodynamic environment to suit the purpose of a particular closure device application. Various embodiments of the present invention may be advantageous in that they may solve or reduce one or more of the potential problems and/or disadvantages discussed above in this paragraph.

It is therefore a principal object and advantage of the present invention to provide specially designed Mg—Al alloys and medical uses thereof in a hemodynamic environment that overcome the problems and disparate findings of the prior art.

In accordance with the foregoing object and advantage, an embodiment of the present invention provides medical devices including closure devices made from such specially designed Mg—Al alloys. The closure device, or closure device implant, for sealing an opening formed through biological tissue can comprise a portion that sits in (or is at least partially exposed to) the lumen of a blood vessel (such as the femoral artery) ("footplate" portion), a portion that plugs the opening and may also be partially be exposed to the lumen of the blood vessel ("plug" portion), and portion that connects the footplate to the plug and may also be at least partially exposed to the lumen of the blood vessel ("wire" portion). It is contemplated that a closure device made from the Mg—Al alloys of the embodiments of the present invention may not contain each and every one of these specific portions. For example, the closure device may include only a wire portion and a plug portion, only a footplate portion and a plug portion, only a footplate portion and a wire portion, or only a footplate portion.

In accordance with an embodiment of the present invention, the specially designed Mg—Al alloys can include Mg—Al alloy compositions comprising Al alloy contents in any range that may result from the "tuning" for a particular purpose of the Mg—Al alloy (preferably within the range of 1 to 10% for the purposes disclosed herein). An amount of Fe can also be added to the Mg—Al alloy composition as a corrosion activator.

In accordance with an embodiment of the present invention, the ability to tune the in vivo corrosion rate of the closure device portion made from a Mg—Al alloy of an embodiment of the present invention by adjusting the Al alloy content of the Mg—Al alloy is provided.

In accordance with an embodiment of the present invention, at least one portion of the closure device can be made from a Mg—Al alloy of an embodiment of the present invention. Not all of the portions of the closure device need to be made from a Mg—Al alloy of an embodiment of the present invention. At least two of the portions of the closure device can be made from the same Mg—Al alloy of an embodiment of the present invention. Alternatively, in order to tune the corrosion rates of the particular portions of the closure device, the portions of the closure device can be made from different Mg—Al alloys of an embodiment of the present invention. For example, in order to tune the footplate to corrode at a greater rate than the plug, the footplate can be made from a Mg—Al alloy with a greater Al content percentage than the plug. Also, as understood by those skilled in the art, metallic corrosion is a surface phenomenon. By adjusting the surface area-to-volume ratio of the various closure device portions/components, the overall time for complete portion/component corrosion can be varied, or "tuned", to accommodate different residence times. While the corrosion rate of the material remains consistent (where, for example, the components are made from the same alloy), the topography of the individual components may be varied to provide greater or lesser surface area at which corrosion may occur, therefore providing faster overall component corrosion (and therefore shorter residence time in vivo) or slower overall component corrosion (and therefore longer relative residence time in vivo), respectively. In a preferable embodiment, the footplate is designed to have a greater surface area to volume ratio than the plug, thus resulting in a shorter residence time in vivo as compared to the plug.

As discussed more fully in the Detailed Description section below, the corrosion rate and biocompatibility of specially designed magnesium alloys with Al contents ranging from 1 to 8.25 wt. % were assessed using in vivo exposure to support the development of a novel percutaneous vascular closure device implants. The closure device implant is intended to stop bleeding in wounds associated with arteriotomies rapidly and completely by deploying a small implantable closure device implant delivered using a specially designed tool inserted into the wound. In this application, it is intended that the closure device implant be gradually absorbed over hours and days as natural healing takes place. This performance objective requires that a balance be struck between material corrosion rate (which is high in the overall context of bioimplanted metals), and wound healing rate. This contrasts the high corrosion resistance design objective, which is more common for implant materials.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
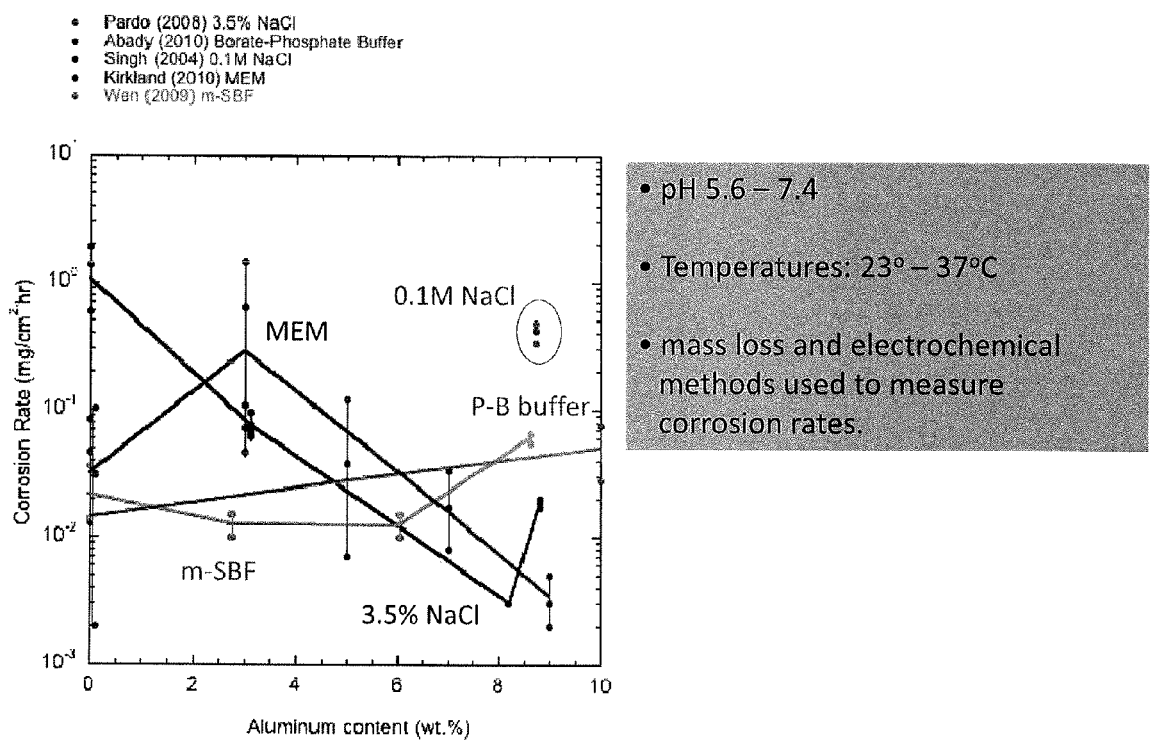
FIG. 1 is a graphical illustration showing that Mg corrosion rates in biological-stimulated environments have been shown to be affected by Al additions, albeit with apparent disparate results.

Reference will now be made in detail to the present preferred embodiments of the invention, examples of which are illustrated in the accompanying drawings.

In accordance with an embodiment of the present invention, closure device implants, such as the closure device implant shown and described in U.S. Pat. Pub. No. 20110046665 (which is incorporated by referenced herein in its entirety), can be made from the specially designed Mg—Al alloys of embodiments of the present invention. An embodiment of the closure device implant of U.S. Pat. Pub. No. 20110046665 is shown therein in its completely deployed configuration and position in FIG. 42. The closure device implant as shown in FIG. 42 of U.S. Pat. Pub. No. 20110046665 includes a footplate 110', a plug 111, and a wire 120. FIG. 42 also shows subcutaneous tissue 409 overlying a blood vessel 400, outside surface 402 and an inside surface 403 of a blood vessel wall 401 of the blood vessel 400. The closure device implant is shown sealing the opening/arteriotomy 405. Many other embodiments of the closure device implant, and of the closure device deployment device (see e.g., reference numeral 200, FIG. 53(a)), are shown and described in U.S. Pat. Pub. No. 20110046665 and are a part of certain embodiments of the present invention.

Figure 2:
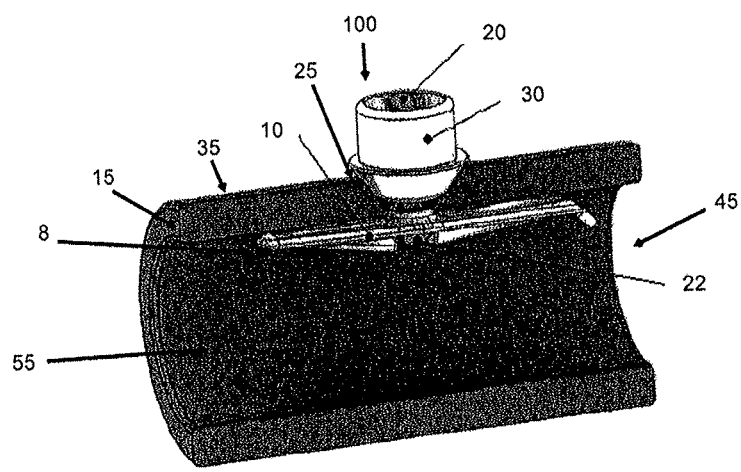
FIG. 2 is a perspective view of a closure device embodiment in a post-deployed arteriotomy sealing position and configuration that can be made from the specially designed Mg—Al alloys of embodiments of the present invention.

Another embodiment of the closure device implant can be made from the specially designed Mg—Al alloys of embodiments of the present invention includes the closure device implant 100 shown in FIG. 2. FIG. 2 shows a closure device implant including one or more of the following components—a footplate 10 which is seated on the inside surface 5 of the blood vessel wall 15 of a blood vessel 45 (blood vessel 45 is shown sectioned along its longitudinal axis in order to show the lumen 55), a plug 30 sealingly positioned within the arteriotomy 25, and a wire 20 connecting the footplate 10 with the plug 30, the wire 20 including a ball and socket connection at its distal end with the footplate and a plastically deformed bed at its proximal end securing the plug with the footplate. FIG. 2 illustrates the clamping of the arteriotomy 25 between the plug 30 and the footplate 10, preferably giving a stable construct and immediate hemostasis, according to an embodiment of the present invention.

It is contemplated that other existing (or as yet to exist) closure device-type implants can be made from the specially designed Mg—Al alloys of embodiments of the present invention. If a portion of a device that is used to seal an opening formed through a blood vessel is exposed to blood in the lumen of a blood vessel and biocompatibility and a particular corrosion rate is desired, the device can be made from the specially designed Mg—Al alloys of embodiments of the present invention. Such devices are shown and described in, for example, U.S. Pat. Nos. 4,744,364, 5,222,974, 5,282,827, 5,441,517, 5,676,689, 5,861,004, 6,045,569, 6,007,563, 6,090,130, 5,545,178, 5,531,759, 5,593,422, 5,916,236, 6,890,343, and 6,969,397, all of which are hereby incorporated by reference herein in their respective entirety(ies).

Advantages of the invention are illustrated by the Examples Section, below. However, the particular materials and amounts thereof recited in these examples, as well as other conditions and details, are to be interpreted to apply broadly in the art and should not be construed to unduly restrict or limit the invention in any way.

The Examples Section describes the in vivo evaluation of the corrosion rate, corrosion mode and biocompatibility of Mg—Al alloys in a hemodynamic environment. An objective of the described studies is to select an Mg—Al alloy for a closure device implant that is entirely biocompatible and rapidly bioabsorbable. Short terms goals include the creation of a closure device implant that facilitates immediate hemostasis upon deployment, causes a minimal, if any, acute inflammatory response, avoidance of embolisms, and allows for accelerated patient ambulation. Long term goals include rapid and complete bioabsorption of at least the intraluminal footplate component (approx. 1-2 days), wound healing, no loss of vessel patency, and no deleterious systemic effects from chemical exposure (e.g., corrosion byproducts, hydrogen evolution).

EXAMPLES

Example 1

AZ31 Implant Material

This Example describes the implanting of a footplate made from AZ31 in a sheep aorta, in order to study the corrosive effects of this hemodynamic environment on such a magnesium alloy.

Figure 3:
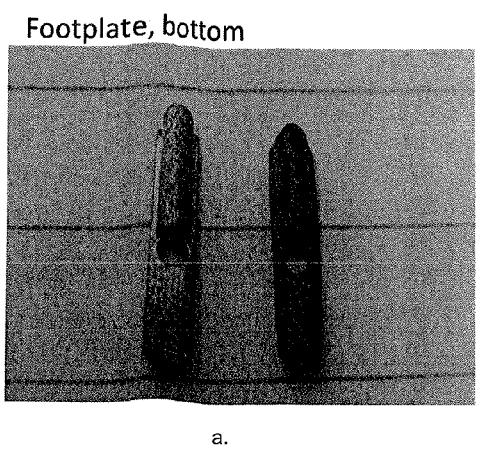
FIG. 3(a)-(b) show pictures of the results of a 15-day explant, sheep aorta (retroperitoneal approach) vs. an uncorroded specimen.
Figure 3:
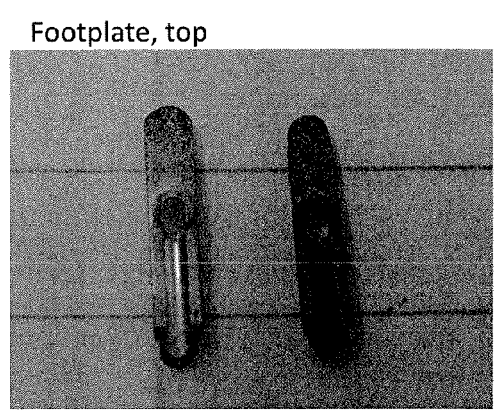

FIG. 3(a)-(b) show pictures of the results of a 15-day explant, sheep aorta (retroperitoneal approach) vs. an uncorroded specimen. FIG. 3(a) shows the bottoms of the respective footplates, and FIG. 3(b) shows the tops of the respective footplates, where the uncorroded footplate specimen is positioned on the left hand side in each of FIGS. 3(a) and 3(b). It is estimated that the time to complete absorption would be approximately 150 days.

An aim of the following Example is to characterize the effect of Al content on the alloy dissolution rate in a physiological hemodynamic environment. The biocompatibility of Mg is known, but a more rapid bioabsorption rate is an objective for the closure device implant embodiments.

Example 2

This Example describes an in vivo study undertaken to determine bioabsorption kinetics by corrosion of certain Mg—Al alloys. The study was performed in vivo in sheep femoral arteries; an analog to the human femoral model as it has similar blood flow conditions, similar blood chemistry, similar lumen and arterial wall physiology, and similar endothelial physiology. Also, the pathological tissue reaction to the implants is similar to that in humans. The animals used in this study (animal G3924—sacrificed at 8 hrs.; animal G3918—sacrificed at 4 hours) were 2+ years old, and 200+ lbs.

In brief, small cylindrical Mg alloys samples measuring 0.74 mm in diameter and 5.1 mm in length were implanted in the femoral arteries of sheep (cut-down procedure) using an 18-gauge access needle, and secured to the vessel wall by a single suture. In this way, samples were exposed to environmental effects associated with live blood flow and chemistry, vessel contraction, vessel wall texture, and endothelia growth in a manner consistent with the operation of the vascular closure device.

Five different alloys were studied. The Mg alloy samples included AZ31 as a commercial alloy control. The remaining alloys possessed Mg—Al—Fe ternary compositions. Alloy chemistry and surface preparation were used to modulate corrosion rates. Transition metals including the Al alloy contents ranged from 1 to 8.25 wt. %, as shown in Table 1 below. A small amount of Fe was added to the alloys as a corrosion activator. Transition metals including Fe are strong corrosion activators of Mg corrosion. Al and Zn additions allow mechanical properties to be varied. Al and Zn additions to Mg do not significantly affect corrosion rate of Mg in dilute chloride solutions. See Joseph R. Davis, Metals Handbook, FIG. 1 (showing a graphical illustration of the effect of alloying and contaminant metals on the corrosion rate of magnesium as determined by alternate immersion in 3% NaCl solution).

TABLE 1

Special Mg—Al—Fe Alloys Were Cast and Drawn for In Vivo Corrosion Rate Studies

| Alloy | Al (wt. %) | Fe (wt. %) |
|---|---|---|
| 1. | 1.06 - Mg1Al or Mg1.06Al | <0.01 |
| 2. | 2.94 - Mg3Al or Mg2.94Al | 0.07 |
| 3. | 6.09 - Mg6Al or Mg6.09Al | 0.07 |
| 4. | 8.25 - Mg8Al or Mg8.25Al | 0.05 |
| AZ31 | 3.0 - | (1.0 Zn) |

The samples were then chemically treated in either a ferrous-sulfate-modified sulfuric acid or acetic acid solution. Samples were treated, for example, in an aqueous solution of 1 g of 98% sulfuric acid $H_2SO_4$ and 0.04 g $FeSO_4$ in 10 mL of distilled water for 2 minutes to enrich the surface with Fe and transition metal impurities. This surface treatment was carried out in an attempt to further stimulate corrosion.

Figure 9:
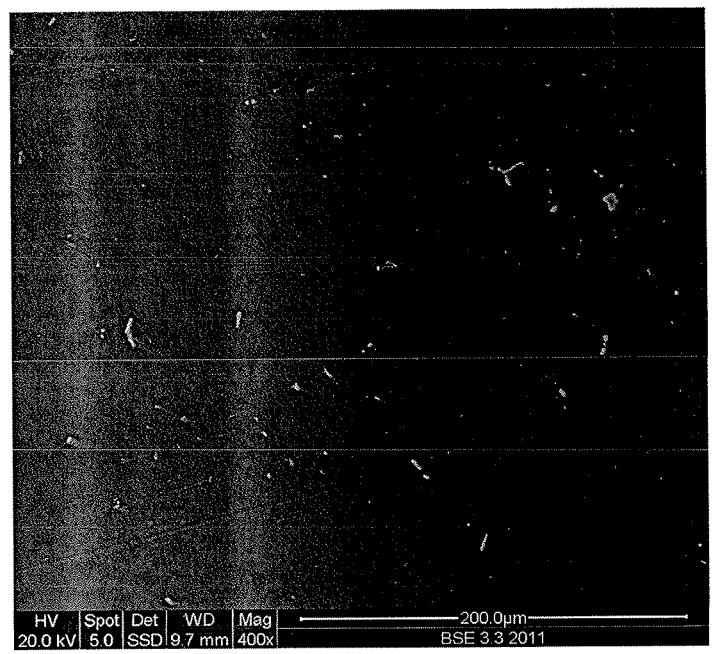
FIG. 9 is an SEM image showing transition metal-rich intermetallic particles (Al with Mg background and trace amounts of Fe) evenly dispersed through the constituent experimental alloys.

FIG. 9 is a scanning electron micrograph (SEM) image showing a polished cross section of the Mg—Al—Fe alloy, according to an embodiment of the present invention. Impurity elements and transition metals such as Fe and Mn (which may be impurities themselves) are concentrated in these particles. Particles of this type are important initiation sites for corrosion in Mg alloys and may be considered activating sites for corrosion. Having a dispersion of corrosion initiation sites is important for achieving a high corrosion rate and ensuring that the corrosion remains more or less uniform across the component surface. The transition metal-rich intermetallic particles shown have a basically consistent, even, and homogenous dispersion through the experimental alloys. This dispersion, as discussed in the results section below, results in a basically even corrosion rate—a uniform corrosion behavior.

Six implants were added per femoral artery; 1 cm apart (1 of each of 4 Mg—Al—Fe plus two AZ31 as controls).

Figure 4:
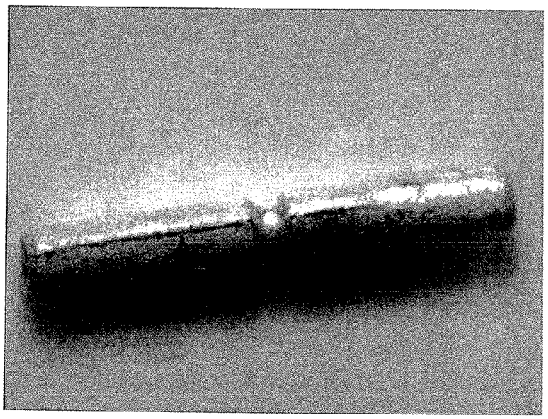
FIG. 4 shows a picture of one of the implant specimens prior to implantation into a sheep femoral artery, according to an embodiment of the present invention.

FIG. 4 shows a picture of one of the implant specimens prior to implantation into a sheep femoral artery, according to an embodiment of the present invention.

Figure 5:
FIG. 5 shows a picture of the anterior exposure, post implantation into a sheep femoral artery, according to an embodiment of the present invention.

FIG. 5 shows a picture of the anterior exposure, post implantation into a sheep femoral artery, according to an embodiment of the present invention.

Figure 6:
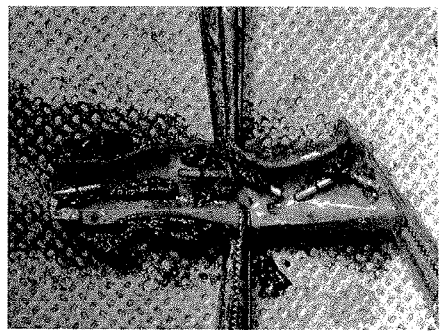
FIGS. 6(a)-(d) shows ex vivo gross histology of (a) the left femoral artery after 4 hours of implantation, (b) the left femoral artery after 8 hours of implantation, (c) the right femoral artery after 4 hours of implantation, and (d) the right femoral artery after 8 hours of implantation.
Figure 6:
Figure 6:
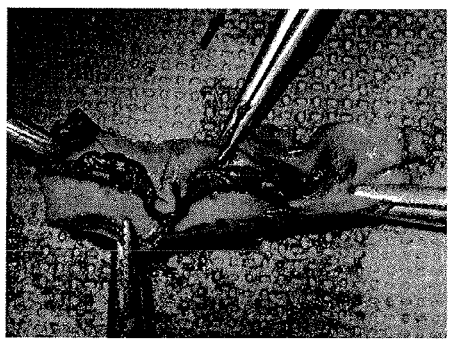
Figure 6:
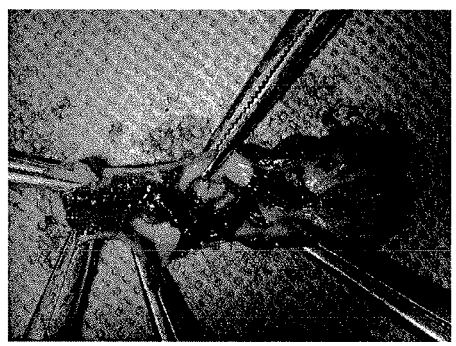

FIGS. 6(*a*)-(*d*) shows ex vivo gross histology of (a) the left femoral artery after 4 hours of implantation, (b) the left femoral artery after 8 hours of implantation, (c) the right femoral artery after 4 hours of implantation, and (d) the right femoral artery after 8 hours of implantation.

Figure 7:
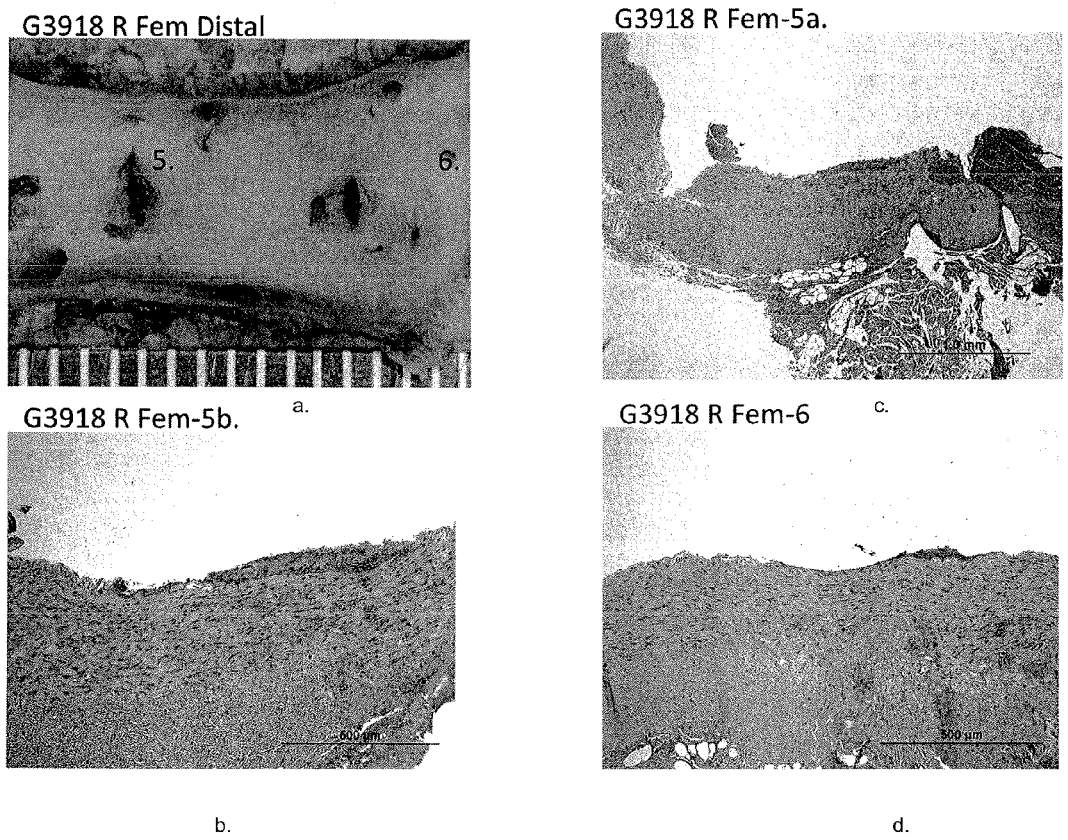
FIG. 7 (a)-(d) shows the histopathology of portions of the sheep (animal G3918) femoral arteries, showing little to no inflammatory reaction, according to an embodiment of the present invention.

FIG. 7 (*a*)-(*d*) shows the histopathology of portions of the sheep (animal G3918) femoral arteries, showing little to no inflammatory reaction, according to an embodiment of the present invention.

Tables 2 and 3, below, show the weight loss analysis of the sheep implants made from the alloys set forth in Table 1.

TABLE 2

Animal G3924, Sacrificed at 8 hours

| Implant Position Proximal-to-Distal | Alloy | Right Femoral explant weight original weight (g) | % Wt Lost | Left Femoral explant weight original weight (g) | % Wt Lost |
|---|---|---|---|---|---|
| 3 | Mg6Al | .00141 .00358 | 61 | .00256 .00359 | 29 |
| 4 | Mg3Al | .00256 .00345 | 26 | .00288 .00340 | 15 |
| 5 | Mg1Al | .00331 .00338 | 2.0 | .00326 .00332 | 1.8 |
| 6 | Mg8Al | .00050 .00345 | 85.5 | .00191 .00341 | 44 |

TABLE 3

Animal G3918, Sacrificed at 4 hours

| Implant Position Proximal-to-Distal | Alloy | Right Femoral explant weight original weight (g) | % Wt Lost | Left Femoral explant weight original weight (g) | % Wt Lost |
|---|---|---|---|---|---|
| 1 | Mg6Al | .00288 .00357 | 19 | .00295 .00348 | 15 |
| 2 | Mg3Al | .00305 .00348 | 12 | .00304 .00342 | 11 |
| 3 | Mg1Al | .00328 .00333 | 1.5 | .00329 .00333 | 1.2 |
| 4 | Mg8Al | .00259 .00333 | 22 | .00263 .00337 | 22 |

The results show that all of the experimental Mg—Al alloys were completely dissolved within 5 days of exposure, indicating a corrosion rate that is dramatically faster than Mg alloy AZ31, which was scarcely attacked in short-duration exposures. Corrosion rates were found to increase with increasing Al content; a trend that is at odds with at least some of the corrosion rate data reported for Mg—Al alloys in SBF and MEM. In the study carried out by Wen et al., AZ91 was found to corrode at a rate of about 0.01 mg/cm2-hr (See Z. Wen, C. Wu, C. Dai, F. Yang, J. Alloys and Compounds, 488, 392-399 (2009)), while Kirkland et al. found a corrosion rate of 0.004 mg/cm2-hr for Mg-9Al (See N. T. Kirkland, J. Lespagnol, N. Birbilis, M. P. Staiger, Corrosion Sci., 52, 287-291 (2010)).

Figure 8:
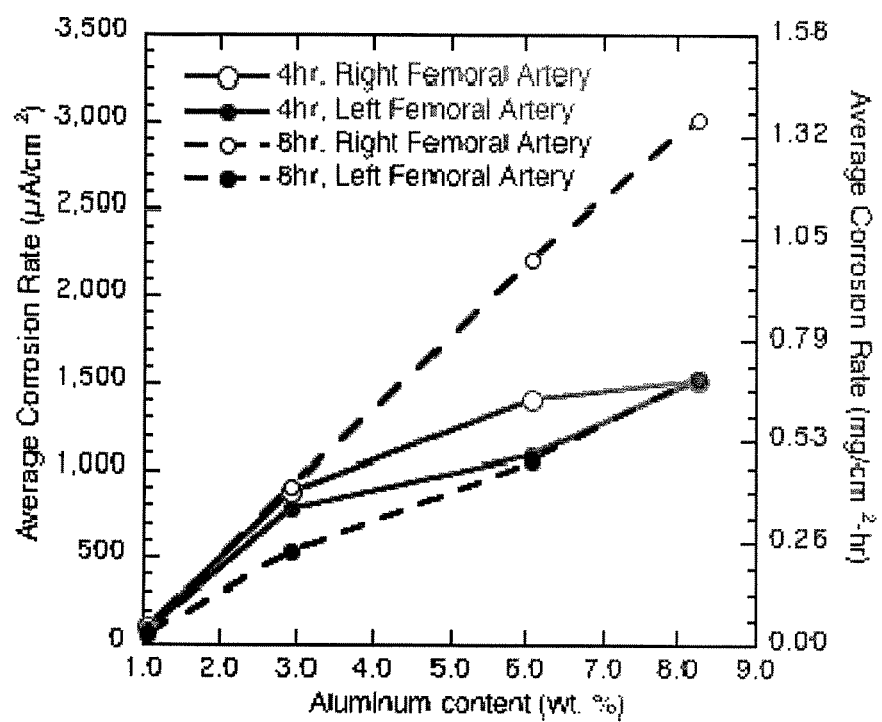
FIG. 8 is a graphical illustration showing the in vivo corrosion rate versus Al content for the Mg—Al—Fe alloys examined by mass loss, according to an embodiment of the present invention.

FIG. 8 shows that the corrosion rate for surface treated Mg-8.25Al exposed in vivo corrode at rates ranging from 0.6 to 1.3 mg/cm2-hr, which is about 2 orders of magnitude faster than in quiescent simulated in vitro environments. The results show a strong dependence of corrosion rate on Al content, and corrosion rates that are suitable for closure device implant applications.

Figure 10:
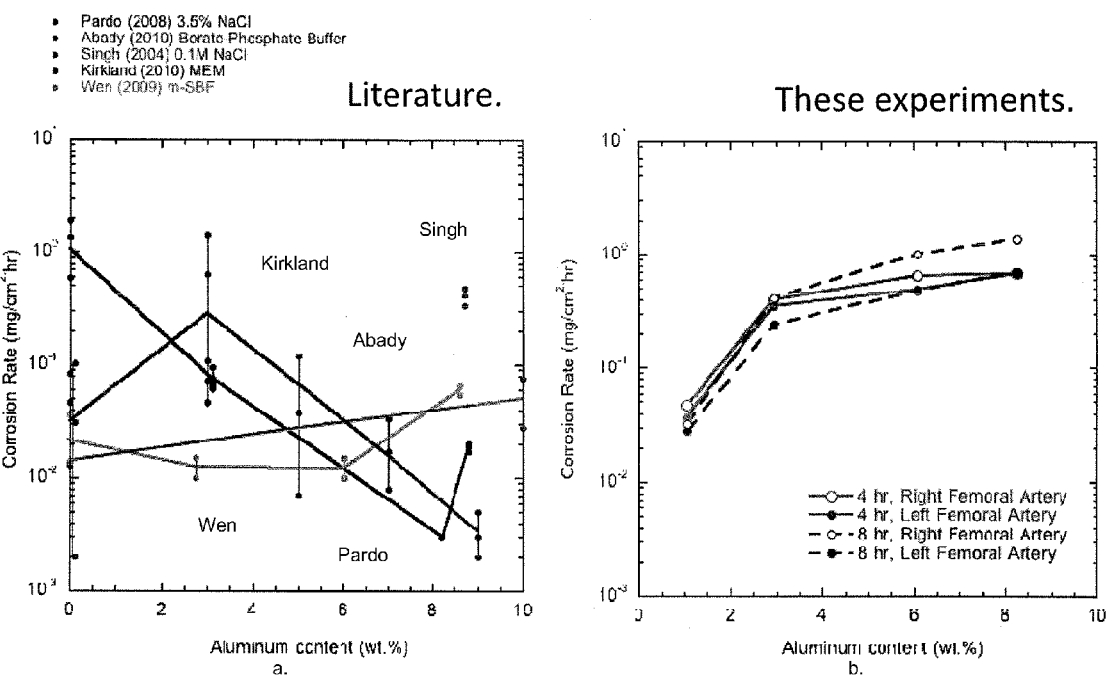
FIGS. 10(a)-(b) show a comparison of corrosion rates in bio-environment stimulants, in the existing literature vs. hemodynamic exposure, according to an embodiment of the present invention.

FIGS. 10(*a*)-(*b*) show a comparison of corrosion rates in bio-environment stimulants, as discussed in some of the referenced existing literature vs. hemodynamic exposure, according to an embodiment of the present invention.

Figure 11:
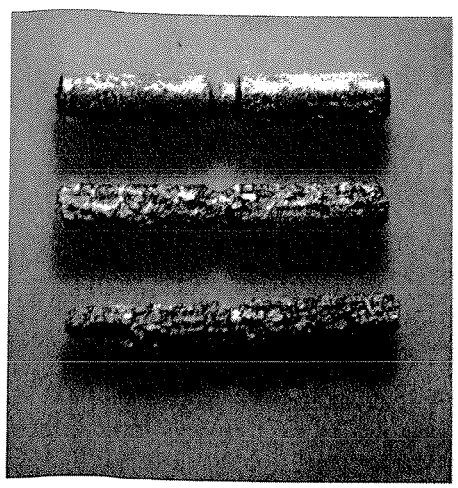
FIG. 11 is an optical micrograph of explanted Mg alloy samples showing the extent of corrosion, according to an embodiment of the present invention. AZ31 after 8 hours (is shown at the top), Mg-8.25Al after 4 hours exposure (is shown at the middle), and Mg-8.25Al after 8 hours exposure (is shown at the bottom).

In terms of corrosion morphology, the attack observed is essentially uniform in nature (uniform localized corrosion). Corrosion of the experimental Mg—Al—Fe alloys was rapid relative to AZ31. FIG. 11 is an optical micrograph of explanted Mg alloy samples showing the extent of corrosion. AZ31 after 8 hours (is shown at the top), Mg-8.25Al after 4 hours exposure (is shown at the middle), and Mg-8.25Al after 8 hours exposure (is shown at the bottom).

Dark corrosion product, which is presumably mixed Mg and Al hydroxide is evident in histological examination of explanted arterial segments. There is no indication of negative immune response; even in separate longer-term studies lasting tens of days. Indeed, separate studies of the closure device implant and its components show endothelialization of Mg alloy components and good wound closure and healing.

These results indicate that the specially designed Mg—Al alloys demonstrate corrosion rates in a hemodynamic environment that will result in bioabsorption of the Mg based components of embodiments of the closure device implant in timeframes (preferably approx. 1-2 days, and up to five days) that are appropriate for the application. The results also suggest the ability to tune the in vivo corrosion rate significantly by adjusting the Al alloy content of Mg—Al—Fe alloys. This tuning can be done depending upon need.

Example 3

Surface Pretreatment of Magnesium and Magnesium Alloys for Tailoring Corrosion Rate This Example describes the modification of magnesium and magnesium alloy surfaces to increase, temporarily or permanently, the dissolution rate for in vivo environments.

In brief, the process involves contacting the alloy with a specially prepared aqueous solution by dipping, spraying or brushing followed by rinsing and drying in clean water. The solution composition is defined by the addition of a suitable acid to activate the alloy and modify the pH of the solution, and an accelerant, which is specifically selected to achieve increased corrosion. Through this process, the surface composition of the alloy is modified by (1) enriching it in impurities already contained in the alloy as the Mg component corrodes preferentially, and (2) depositing product(s) from solution that are associated with the acid and accelerant addition.

Suitable inorganic acids include sulfuric, nitric, hydrochloric and phosphoric and phosphonic. Acid concentrations may range from 1 mg to 10 g per liter of solution. Suitable organic acids include citric, tartaric, acetic and oxalic. Suitable accelerants are generally soluble transition metal salts, typically though not exclusively of iron, manganese, and cobalt. Accelerant concentrations are typically much less than acid concentrations and range from 0.01 mg to 1 g per liter of solution.

The contact time between solution and treated surface may be varied to further adjust corrosion rate. Contact times may range from 5 seconds to 10 minutes based on the chemistry of the pretreatment solution and the desired corrosion rate. After pretreatment, surfaces are rinsed thoroughly with distilled or deionized water to halt the interaction between the pretreatment solution and the alloy. No further treatment of the surface is needed prior to use. The following is an example of the process.

Mg alloys samples were pretreated by immersion in an aqueous solution of 1 g of 98% sulfuric acid $H_2SO_4$ and 0.04 g of ferrous sulfate $FeSO_4$ in 10 mL of distilled water. Samples were treated in batches of 25 by alloy type for a minimum of 90 seconds and no longer than 120 seconds. Samples were rinsed and dried in air after immersion in the pretreatment solution. Sample batches were weighed before and after pretreatment. Mass losses were calculated and per sample mass losses were estimated as shown in the following Table 4.

TABLE 4

| | Initial | Final | Chang | Initial per sample | Change per sample | Pct. |
|---|---|---|---|---|---|---|
| AZ 31B | 96.4 | 90.3 | 6.1 | 3.9 | 0.24 | 6.3% |
| Mg-1Al | 91.7 | 84.8 | 6.9 | 3.7 | 0.28 | 7.5% |
| Mg-3Al | 89.4 | 85.8 | 3.6 | 3.6 | 0.14 | 4.0% |
| Mg-5Al | 84.5 | 75.7 | 8.8 | 3.4 | 0.35 | 10.4% |
| Mg-8Al | 88.3 | 76.8 | 11.5 | 3.5 | 0.46 | 13.0% |

The results show that mass loss increases regularly for the Mg-3Al, Mg-6Al and Mg-8Al samples from 0.14 to 0.46 mg per sample. This response is consistent with the expectation that Mg—Al alloy dissolution rate increases with increasing Al content. The mass losses for AZ31 and Mg-1Al samples were 0.24 and 0.28 mg per sample and appear out of the trend presented by the other samples. These two batches of samples were exposed to the pretreatment solution for times longer than 90 seconds due to difficulty in removing and washing the very small samples. The pretreatment protocol was refined for the Mg-3Al, Mg-6Al and Mg-8Al samples and their immersion times were very close to the 90 second target. All of the samples except the AZ31B samples presented bright lustrous surfaces after pretreatment. The AZ31B samples were slightly darkened.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A closure device implant for sealing an opening formed through a blood vessel, said closure device comprising:
    a footplate portion at least partially exposed to the lumen of the blood vessel when in use; and
    wherein said footplate portion is formed of a biocorrodible metal comprising a magnesium alloy formulated with a corrosion activator comprising between 0.01% and 0.08% iron, wherein said footplate portion's magnesium alloy comprises between about 1% to 8.25% aluminum, wherein said magnesium alloy formulated with the corrosion activator is formulated to have a faster corrosion rate in a hemodynamic environment than a corrosion rate of AZ31.

2. The closure device implant of claim 1, wherein said footplate portion's magnesium alloy comprises a magnesium alloy selected from the group consisting of Mg1.06Al, Mg2.94Al, Mg6.09Al, and Mg8.25Al.

3. The closure device implant of claim 2, further comprising a plug portion connected to said footplate portion.

4. The closure device implant of claim 3, wherein said plug portion is formed of a biocorrodible metal comprising a magnesium alloy formulated with a corrosion activator, wherein said plug portion's magnesium alloy comprises between about 1% to 8.25% aluminum.

5. The closure device implant of claim 4, wherein said plug portion's magnesium alloy comprises a magnesium alloy selected from the group consisting of Mg1.06Al, Mg2.94Al, Mg6.09Al, and Mg8.25Al.

6. The closure device implant of claim 5, wherein said footplate portion's magnesium alloy and said plug portion's magnesium alloy comprise different percentages of aluminum.

7. The closure device implant of claim 5, wherein said footplate portion's magnesium alloy and said plug portion's magnesium alloy comprise the same percentages of aluminum.

8. The closure device implant of claim 4, wherein said plug portion's magnesium alloy further comprises between 0.01% and 0.08% iron.

9. The closure device implant of claim 2, wherein said footplate portion's magnesium alloy is Mg8.25Al.

* * * * *